US005786194A

United States Patent [19]
Dunlap

[11] Patent Number: 5,786,194
[45] Date of Patent: Jul. 28, 1998

[54] PERIPLASMIC 3':5'-CYCLIC NUCLEOTIDE PHOSPHODIESTERASE AND RELATED METHODS FOR PRODUCING AND USING THE SAME

[75] Inventor: Paul Vernon Dunlap, Woods Hole, Mass.

[73] Assignee: Woods Hole Oceanographic Institute, Woods Hole, Mass.

[21] Appl. No.: 369,130

[22] Filed: Jan. 5, 1995

Related U.S. Application Data

[62] Division of Ser. No. 4,751, Jan. 13, 1993, Pat. No. 5,382,519.

[51] Int. Cl.$^6$ ............................. C12N 9/16; C12N 15/55
[52] U.S. Cl. .................................. 435/196; 536/23.2
[58] Field of Search ........................... 435/196; 536/23.2

[56] References Cited

U.S. PATENT DOCUMENTS 5,082,785   1/1992   Manning ......................... 435/252.32

OTHER PUBLICATIONS

Alper & Ames, *Journal of Bacteriology*, 122:1081–1090 (1975).
Ames et al., *Journal of Bacteriology*, 160:1181–1183 (1984).
Barfield et al., Microbiol. Enzymes in Aquatic Environment, Springer Berlay, pp. 239–248 (1991).
Beacham et al., *J. Gen. Micro.*, 119:31–34 (1980).
Botsford, *Journal of Bacteriology*, 160:826–830 (1984).
Botsford, *Microbiological Review*, 45:620–642 (1981).
Buettner et al., *Journal of Bacteriology*, 114:1068–1073 (1973).
Bullock et al., *Biotechniques*, 5:376–379 (1987).
Devroetes, *Science*, 245:1054–1058 (1989).
Dunlap et al., *J. Gen. Microbiol.*, 138:115–123 (1992).
Francko, *Advances in Cyclic Nucleotide Research*, pp. 97–117 (1983).
Bengis–Garber, *Can. J. Microbiol.*, 31:543–548 (1985).
Monard et al., *Biochemical and Biophysical Research Communications*, 35:584–591 (1969).
Robison et al., Cyclic Amp, Academic Press, New York (1971).
Ruby et al., *Biol. Bull.*, 151:574–586 (1976).
Saier et al., *J. of Biological Chemistry*, 250:7593–7601 (1975).
Sambrook et al., Molecular Cloning, Cold Spring Harbor Laboratory, (1989).
Sanger et al., *Proc. Natl. Acad. Sci.*, 74:5463–5467 (1977).
Silhavy et al., Experiments with Gene Cloning, Cold Spring Laboratory (1986).
Simon et al., *Meth. Enzymol.*, 118:640–659 (1986).
Ullman et al., Advances in Cyclic Nucleotide Research, 15:1–52 (1983).
Young et al., *Proc. Natl. Acad. Sci.*, 80:1194–1198 (1983).
Lacombe et al., *J. Biol. Chem.*, 261:16811–16817 (1986).
Callahan et al., Abstracts of the General Meeting of the American Society for Micrbiology, p. 269 (1993).
Dunlap et al., Abstracts of the General Meeting of the American Society for Microbiology, p. 269 (1993).
P.V. Dunlap et al., "Growth of the Marine Luminous Bacterium *Vibrio fischeri* on 3':5'–Cyclic AMP: Corrrelation with a Periplasmic 3':5'–Cyclic AMP Phospodiesterase", J. Gen. Microbiol. 138(1) 115–123, Jan. 1992.

*Primary Examiner*—Rebecca E. Prouty
*Attorney, Agent, or Firm*—Linda M. Buckley; Peter F. Corless; David S. Resnick

[57] ABSTRACT

Novel substantially pure periplasmic 3':5'-cyclic nucleotide phosphodiesterases are provided which are obtainable from gram negative bacterium capable of growing on restricted media containing cAMP or cGMP as a sole carbon source. Also provided is the isolated DNA coding for such enzymes and related methods of producing the same.

4 Claims, 4 Drawing Sheets

FIG. 1

SDS-PAGE OF ACETONE PURIFICATION OF CpdP PROTEIN

```
  1  AGTAGAACTATCAAATTCTGTGGAGCATACCGCTTATAATTACCTTCTTATCAATAGTCTTAAATATTAATACATC

78  ATTCATTTATCTCATTGTATTATCTGATTGAGCACAAGGGTGTGCAGTATTATTTAAGGTTGGAT
                      -10                                    SD

152  AAT TTA GCA GTG TTA TTT ACG TGT TTG TCT GTA TTT TCT ATG TTT AAA
     Asn Leu Ala Val Leu Phe Thr Cys Leu Ser Val Phe Ser Met Phe Lys

203  CAA TCT→GGG AGT TTT GAT ACC GTT TTA ACG TCT AAA TTT GGG TCG GCT
     Gln Ser Gly Ser Phe Asp Thr Val Leu Thr Ser Lys Phe Gly Ser Ala

254  GAT GGT AAT TTA GCT TTT TTA ATT AAA AGT AGT GAG GAT TCT AAT CAA
     Asp Gly Asn Leu Ala Phe Leu Ile Lys Ser Ser Glu Asp Ser Asn Gln

305  GTT ATG CTT GAT TCT TTT GTT GTC AAT GGA GTT TTA ATT TCA TAC TCA TTT
     Val Met Leu Asp Ser Phe Val Val Asn Gly Val Leu Ile Ser Tyr Ser Phe

356  AAA GGA TTT AAA GAT ATT AAG ACC AGG GAT ATT ATT ACA TTT AGT GAG CAG
     Lys Gly Phe Lys Asp Ile Lys Thr Arg Asp Ile Ile Thr Phe Ser Glu Gln

407  GTA GGT CTA TTA GTT GGA TCT TAC TCG TTT CCT ATT AGT GAT TAC AGT GCT
     Val Gly Leu Leu Val Gly Ser Tyr Ser Phe Pro Ile Ser Asp Tyr Ser Ala

458  CAT TTA GAC CAT GTT GGT GCT TTA CCT TTT CTT CCT ATT GAT GAC AAA
     His Leu Asp His Val Gly Ala Leu Pro Phe Leu Pro Ile Asp Asp Lys

509  AAA CCG ATA TAT GGA GCA TTA GCA AAA GAT CTC ATG AAG AAA TAC AAA
     Lys Pro Ile Tyr Gly Ala Leu Ala Lys Asp Leu Met Lys Lys Tyr Lys

560  TTT AAT TGG TCA GCA AAT TTT CCT AAT AAA AAC GGT GAA GGC TTT AAA
     Phe Asn Trp Ser Ala Asn Phe Pro Asn Lys Asn Gly Glu Gly Phe Lys

611  CTG AAC TAC TAT AAT GTG CTT GAT CAA CCG GGC GTT TGG AGT CCG GTA
     Leu Asn Tyr Tyr Asn Val Leu Asp Gln Pro Gly Val Trp Ser Pro Val
```

FIG. 4 (CONT.)

| Pos | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 662 | GCT Ala | GAA Glu | ACA Thr | ACA Thr | ATG Met | AGT Ser | GTG Val | GTG Val | TCA Ser | TTG Leu | CCT Pro | TTG Leu | TCT Ser | CAT His | TCT Ser | GGT Gly | GGG Gly |
| 713 | CAA Gln | TCT Ser | ACG Thr | GTA Val | TTT Phe | ATT Ile | CTA Leu | AAA Lys | GAC Asp | AGT Ser | GAA Glu | GGG Gly | GAT Asp | GTA Val | TTT Phe | GCT Ala | TAT Tyr |
| 764 | TTT Phe | GGT Gly | GAT Asp | ACA Thr | GGA Gly | CCT Pro | GAT Asp | GTA Val | GTA Val | GAG Glu | AAA Lys | AGC Ser | TCG Ser | GCA Ala | ATG Met | AGG Arg | ACT Thr |
| 815 | GCA Ala | TGG Trp | TCT Ser | GTT Val | TTA Leu | GCT Ala | CCT Pro | TTT Phe | GTA Val | GTA Val | CAA Gln | AAA Lys | GGG Gly | AAG Lys | TTA Leu | GGG Gly | ATT Ile |
| 866 | ATT Ile | GAA Glu | GTT Val | CCA Pro | TTT Phe | TTT Phe | AAC Asn | AAC Asn | GAA Glu | AAA Lys | ACC Thr | GAT Asp | CCA Pro | TTA Leu | TCT Ser | TTT Phe | GGA Gly |
| 917 | CAC His | TTA Leu | ACG Thr | CCA Pro | TGG Trp | TTA Leu | GTT Val | GTT Val | AAA Lys | CTA Leu | TTA Leu | GTA Val | AGT Ser | CTT Leu | GAA Glu | GAC Asp | ATG Met |
| 968 | AAT Asn | GGC Gly | AAA Lys | GGC Gly | TTA Leu | AAT Asn | GAT Asp | AAT Asn | GTA Val | GAA Glu | GTA Val | GCC Ala | ATA Ile | AGC Ser | CAC His | ATC Ile | AAA Lys |
| 1019 | TAC Tyr | AGC Ser | TTA Leu | AAG Lys | AAT Asn | AGT Ser | GAT Asp | CCT Pro | AAA Lys | GAT Asp | GAA Glu | ATT Ile | ATT Ile | AAA Lys | AAA Lys | CAG Gln | TTA Leu |
| 1070 | GTA Val | GAA Glu | GTA Val | AAT Asn | GAC Asp | TTA Leu | GTA Val | GTA Val | ATT Ile | TTC Phe | TTT Phe | CCT Pro | GAG Glu | CAA Gln | GGT Gly | GAT Asp |
| 1121 | TCA Ser | TTG Leu | CAG Gln | TTT Phe | TAA *** | AAAAGTCATTGTAAAAGTGGATATGTCAATACAAAGACCATATCCAC |
| 1184 | GGATTTGTTTTTATCTCTTAAATCGTCGTTTCTATCTTTTTAAGCACGGCGATCTCATTGGGTACATCAATGTT |

5,786,194

PERIPLASMIC 3':5'-CYCLIC NUCLEOTIDE PHOSPHODIESTERASE AND RELATED METHODS FOR PRODUCING AND USING THE SAME

This is a divisional of application Ser. No. 08/004,751 filed on Jan. 13, 1993, now U.S. Pat. No. 5,382,519.

The present invention relates to a novel, substantially pure 3':5'-cyclic nucleotide phosphodiesterase which is found in the periplasm of certain bacteria, and which confers on those bacteria the ability to grow on, e.g., cAMP or cGMP as a sole carbon source. The present invention also relates to recombinant 3':5'-cyclic nucleotide phosphodiesterase, to isolated DNA encoding that enzyme, as well as to vectors, transformed hosts and methods for producing the recombinant enzyme.

3':5'-cyclic AMP (cAMP), a regulatory molecule involved in controlling gene transcription in various bacteria and in hormonally regulated processes in eucaryotic organisms, is synthesized from ATP by adenylate cyclase (E.C.4.6.1.1) and is degraded to 5'AMP (AMP) by cAMP phosphodiesterase (E.C.3.1.4.17) (Robison et al., *Cyclic Amp*, Academic Press, New York (1971); Botsford, Microbiological Reviews, 45:620–642 (1981); Francko, Advances in Cyclic Nucleotide Research, pp. 97–117 (1983); Ullman & Danchin, Advances in cyclic Nucleotide Research, 15:1–52 (1983); Devroetes, Science, 245:1054–1058 (1989)). In enteric bacteria, cellular levels of cAMP apparently are regulated by the expression and activities of these two enzymes, which are cytoplasmic, and by excretion of excess cAMP into the growth medium. However, the role of cAMP phosphodiesterase in this regulation has not been completely resolved (Monard et al., Biochemical and Biophysical Research Communications, 35:584–591 (1969); Buettner et al., Journal of Bacteriology, 114:1068–1073 (1973) ; Alper & Ames, Journal of Bacteriology, 122:1081–1090 (1975); Saier et al., Journal of Biological Chemistry, 250:7593–7601 (1975); Botsford, 1981 supra; Botsford, Journal of Bacteriology, 160:826–830 (1984)). Alternatively, cAMP phosphodiesterase might function as a defence against extracellular cAMP, which can cause growth inhibitory and lethal effects in various Gram-negative bacteria. A role in defence against cAMP might require that the enzyme be extracellular in bacteria, as it is in the cellular slime mold *Dictyostelium discoideum*.

In a recent paper, we described the novel ability of the symbiotic bioluminescent bacterium *Vibrio fischeri* to utilize cAMP as a sole source of carbon and energy for growth. This ability correlates with, and apparently depends on, the synthesis by *V. fischeri* of a 3':5'-cAMP phosphodiesterase of exceptionally high activity in the periplasmic space, a novel cellular location for this enzyme (Dunlap et al., J. Gen. Microbiol. 138:115–123 (1992)). The cellular location and high activity of this enzyme in *V. fischeri* indicate that a role for this enzyme in regulation of cytoplasmic cAMP levels is unlikely. These attributes, however, are consistent with a role in defense against extracellular cAMP. Alternatively, the periplasmic CPDase of *V. fischeri* could function in degradation and scavenging of free cAMP (Barfield et al., *Microbiol. Enzymes in Aquatic Environment*, Springer Berlay, 1991, pp. 239–248), or possibly in some aspect of cAMP-mediated biochemical interactions between *V. fischeri* and its animal hosts (Dunlap et al., supra).

It would therefore be desirable to produce commercially useful amounts of 3':5'-cyclic nucleotide phosphodiesterases in a substantially pure form, either from its native source or as a recombinant enzyme. Substantially pure enzyme could be used, e.g., as a component in an assay for determining the presence and/or amount of cAMP or cGMP, or to eliminate cAMP or cGMP from environmental, biological, and biomedical samples containing the same.

SUMMARY OF THE INVENTION

In accordance with the present invention, there is provided a novel, substantially pure periplasmic 3':5'-cyclic nucleotide phosphodiesterase, in particular, 3':5'-cAMP and cGMP phosphodiesterase. This enzyme is obtainable from gram negative bacterium such as *Vibrio fischeri*.

This enzyme has very high specific activity and narrow substrate specificity and confers on its source organism the ability to grow on cAMP or cGMP. Also disclosed are methods for identifying and obtaining such periplasmic proteins from other gram negative bacteria.

The present invention further provides means for obtaining the recombinant enzyme as well as the isolated DNA encoding such 3':5'-cyclic nucleotide phosphodiesterases, as well as recombinant vectors, transformed hosts and methods for producing the recombinant enzyme.

BRIEF DESCRIPTION OF THE DRAWINGS

FIG. 3. Sequencing strategy and partial restriction map of the *V. fischeri* cpdP gene. The large arrow indicates the extent and direction of the cpdP gene. The solid region represents *V. fischeri* MJ-1 chromosomal DNA, and the open regions represent the vector, pMER013. Small arrows indicate the direction and extent of sequences obtained with each primer. The restriction sites are: A, ApaI; I, NciI; G, BglIII; P, SspI; S, SalI; and T, BstI.

FIG. 4. Nucleotide sequence and deduced amino acid (SEQ ID NO: 1) translation of the *V. fischeri* cpdP gene. Possible Pibnow box (−10) and ribosome binding (SD) regions are underlined, as is a twelve base pair inverted repeat adjacent to the location where a −35 region would be expected. The arrow between amino acid residues 22 and 23 indicates the cleavage site for the CpdP leader peptide. A possible rho-independent terminator, with a free energy of −21.2 kcal/mol, at the end of the cpdP coding region is underlined.

DETAILED DESCRIPTION OF THE INVENTION

In accordance with one embodiment of the present invention, substantially pure periplasmic 3':5'-cyclic nucleotide phosphodiesterase, such as 3':5'-cyclic AMP or GMP phosphodiesterase, may be obtained by culturing the source organism, such as *Vibrio fischeri*, and recovering the enzyme from the periplasm of the cell.

The enzyme of the present invention is a periplasmic enzyme which confers on the bacterium in which it is expressed the ability to grow on cAMP or cGMP as a sole carbon source. This periplasmic enzyme is believed to be present in a number of gram negative bacteria, including *Vibrio fischeri* and *Serratia marcescens*. Gram negative bacteria which contain such periplasmic enzymes may be identified by simply culturing the candidate bacterium on minimal media containing cAMP or cGMP as the sole carbon source. Survivors of these cultures may be assayed for the presence of the enzyme as described in Dunlap et al., supra, the disclosure of which is incorporated by reference herein.

One source of this enzyme, *Vibrio fischeri*, which harbors 3':5'-cAMP phosphodiesterase, is available from a number of sources, including the American Type Culture Collection under Accession nos. 7744, 25918, 33765, 33983 and 33984.

For recovering the enzyme of the present invention, the bacterium, such as *V. fischeri*, may be grown using any suitable technique such as those described in Dunlap et al., supra. After the cells have been grown, the periplasmic protein fraction is obtained by, for example, the chloroform shock method described by Ames et al., J. Bacteriol., 160:1181–1183 (1984), the disclosure of which is incorporated by reference herein. One can then isolate the target protein by a number of approaches such as ammonium sulfate precipitation followed by one or more of the following: acetone precipitation, affinity chromatography, anion exchange chromatography and the like.

In general, the protein is at least greater than about 10% pure, preferably greater than about 50% pure, and most preferably greater than about 90% pure compared to that found in the source organism. Percent purity may be determined by, for example, visualization of the protein on SDS-PAGE and quantification thereon by scanning densitometry, thereby indicating the protein's relative percent purity with respect to the presence of any other proteins not eliminated in the purification procedure. Therefore, substantially pure at the 50% level means that the protein accounts for at least half of the total protein present in a sample, and substantially pure at the 90% level means that the protein accounts for at least nine-tenths of the total protein present in a sample. Absolute fold purity can be quantified by determining the specific activity (i.e., the enzymatic activity per mg protein per minute) of the protein at a given step in the purification process with reference to its specific activity in whole cells.

The enzyme of the present invention may also be obtained by recombinant techniques whereby the DNA coding for the enzyme is isolated, inserted into a suitable vector and transformed into a host cell, the host cell being cultured under conditions suitable for expression of the enzyme.

In general, the recombinant enzyme can be obtained from any gram negative bacterium producing it by procedures essentially identical to those described herein (see Example 3), i.e., through the process of isolating the DNA encoding it by the procedures described in Example 3, inserting that DNA into a suitable vector such as pBR322 or pACYC184 or lambda phage-based vectors, transforming or transducing a suitable host cell line such as *E. coli*, and culturing the transformed or transduced host cells under conditions suitable for expression of the enzyme such as on minimal media containing cAMP or cGMP as the sole carbon source.

The following examples are given to illustrate embodiments of the present invention as it is presently preferred to practice. It will be understood that these examples are illustratative, and that the invention is not to be considered as restricted thereto except as indicated in the claims.

EXAMPLE 1

Purification of periplasmic 3':5'-cyclic AMP phosphodiesterase from *V. fischeri* MJ-1. Growth and harvesting of cells.

To obtain the periplasmic 3':5'-cAMP phosphodiesterase protein, a one-liter culture of *V. fischeri* minimal medium (VFM) is prepared, composed of 300 mM NaCl, 10 mM KCl, 50 MM $MgSO_4$, 10 mM $CaCl_2$, 5 mM $NH_4Cl$, 0.3 mM α-glycerophosphate and 50 mM HEPES (N-2-hydroxyethylpiperazine-N'-2-ethanesulfonic acid), pH 7.5, 20 mg ferric ammonium citrate per liter, and glucose (10 mM). The culture was inoculated with 10 ml of VFM-glucose-grown cells at a cell density (optical density at 660 nm, $OD_{660}$) of 0.6 to 0.8. The cells were grown at 28° C. with shaking (50 rpm) to saturation (uncorrected $OD_{660}$ of 1.1), and then allowed to sit without shaking for 2 hrs. The culture was then divided among four 500 ml centrifugation bottles, and the cells were harvested by centrifugation at 10,000 rpm for 5 min at 4° C. in a Sorvall RC-2B centrifuge using a GS rotor.

Chloroform shock.

Periplasmic proteins were released from cells by the chloroform shock method described by Ames at al., supra. The cell pellets were resuspended and combined in a total volume of 50 ml of 10 mM Tris buffer (tris[hydroxymethyl] aminomethane) pH 8.0 (22° C.) in a 250 ml centrifuge bottle. To the cell suspension, 10 ml of chloroform was added, and the suspension was mixed by gentle swirling and inversion and then allowed to sit at room temperature for 15 min with occasional inversion. 100 ml of 10 mM Tris buffer (pH 8.0, 22° C.) was then added, the suspension was mixed gently by inversion, and then centrifuged at 10,000 rpm (4° C.) for 20 min. The aqueous phase (approximately 140 ml to 150 ml) was then removed, taking care to avoid the cell pellet and chloroform.

Ammonium sulfate precipitation.

Sufficient (approximately 250 ml) 50 mM Tris buffer (pH 8.0, 22° C.) was added to the periplasmic extract obtained above to raise its volume to 400 ml. The solution was stirred on ice and ammonium sulfate was added, as described by Cooper, *The Tools of Biochemistry* (1977), to give 30, 50 and 65% saturation, with a 30 min. equilibration for each addition of ammonium sulfate. Proteins precipitating with each of these ammonium sulfate additions were collected by centrifugation at 10,000 rpm (0° C.) for 10 min, followed by resuspension in 10 ml of 10 mM Tris buffer (pH 8.0, 22° C.). In our previous study (Dunlap et al., supra), ammonium sulfate fractionation of periplasmic proteins from *V. fischeri* MJ-1 gave small (approximately 4-fold) purification of the 3':5'cAMP phosphodiesterase that was effective in establishing the substrate specificity of the enzyme.

Affinity chromatography.

The 3':5'-cAMP phosphodiesterase was further purified using dye affinity ligand chromatography. The 65% ammonium sulfate fraction, which contained most of the 3':5'-cAMP phosphodiesterase activity, was applied to a 10 ml disposable Poly-Prep chromatography column (Bio-Rad Laboratories, Richmon, Calif.) containing 1 ml of Cibacron Blue agarose (Sigma Chemical Co., St. Louis, Mo.). The column material had been equilibrated with 100 mM $MgSO_4$ at 4° C. as follows. For hydration, 0.2 g of Cibacron Blue agarose was mixed with 2 ml of deionized water and allowed to sit for 15 min. The hydrated agarose was then trapped on a filter (0.2 µM pore size), washed with 100 ml of deionized water, run dry, washed with 15 ml 100 mM $MgSO_4$, run dry, and then resuspended in 3 ml of 100 mM $MgSO_4$ and loaded into the column. To pack the column, 20 ml of 100 mM $MgSO_4$ was then passed through the agarose, without running the column dry, and the sample was added slowly by applying it down the side of the column. The column was then washed with 5 ml of 1M KCl in 50 mM Tris base (pH 10.3). The 3':5'-cAMP phosphodiesterase was then eluted in 5 ml of the wash solution (1M KCl in 50 mM Tris base) containing 10 mM adenosine. The maximum possible flow rate (approximately 20 ml/hr) was used in all cases. Adenosine was used to elute the 3':5'-cAMP phosphodiesterase from the column (instead of cAMP or AMP) because adenosine inhibited 3':5'-cAMP phosphodiesterase activity effectively and did not contribute phosphate, which would interfere with the assays for 3':5'-cAMP phosphodiesterase enzyme.

Anion exchange chromatography.

To remove salts and to lower the pH of the solution, the Cibacron Blue agarose column eluate was then dialyzed in Spectra/Por membrane tubing (m.w. cutoff 3,500) (Spectrum Medical Industries, Los Angeles, Calif.) (prepared as described by Sambrook et al., *Molecular Cloning*, Cold Spring Harbor (1989)), with three changes (3 hrs each) of 1.5 liters of 10 mM imidazole (pH 6.0) at 4° C., with periodic pH correction using 1N HCl. The dialyzed material was then applied to a 10 ml disposable Bio-Rad Poly-Prep chromatography column containing 1.5 ml of DEAE-Sephacel (Sigma). The choice of pH 6.0 was made based on the calculated pI of 5.49 for the mature protein. The DEAE-Sephacel had been equilbrated with 10 mM imidazole (pH 6.0) at 4° C. as follows. The hydrated column material was washed with deionized water, washed with 0.1N HCl, incubated with 0.1N HCl, gently centrifuged (<500 rpm) to permit the solution to be removed, and then repeatedly resuspended with 10 mM imidazole (pH 7.0) and spun to equilibrate the pH to 6.0. Equilibrated DEAE Sephacel was loaded into the column and packed at 4° C. with 30 ml of 10 mM imidazole at pH 6.0. After applying the same sample to the column and washing with 5 ml of the imidazole buffer, the 3':5'-cAMP phosphodiesterase was eluted with 5 ml of 0.2M Nacl in 10 mM imidazole, pH 6.0. After elution, the 5 ml sample was concentrated to 1 ml using a CentriCell 20 (Polysciences, Inc., Warrington, Pa.) centrifugal ultrafilter (nominal molecular weight cutoff 10,000 Daltons), resuspended in 15 ml of 10 mMol imidazole, pH 6.0, in 20% (w/v) glycerol, and concentrated to 1 ml for storage at −70° C. The maximum possible flow rate (approximately 10 ml/hr) was used in all cases.

Protein assay, 3':5'-cAMP phosphodiesterase assay, and polyacrylamide gel electrophoresis of proteins.

Protein content of samples was determined by the method of Bradford, Analyt. Biochem., 72:248–254 (1977), using bovine serum albumin as the standard and a Coomassie brilliant blue G-520 protein assay reagent (Pierce, Rockford, Ill.) essentially in accordance with the manufacturer's instructions.

Activity of 3':5'-cAMP phosphodiesterase in samples was measured with the method of Cheung essentially as described by Dunlap et al. (1992), supra, using cAMP as the substrate, 5'-nucleotidase to cleave the generated 5'AMP, and with the phosphate released determined by the method of Fiske and SubbaRow (J. Biol. Chem., 66:375–400 (1925)).

Figure 1:
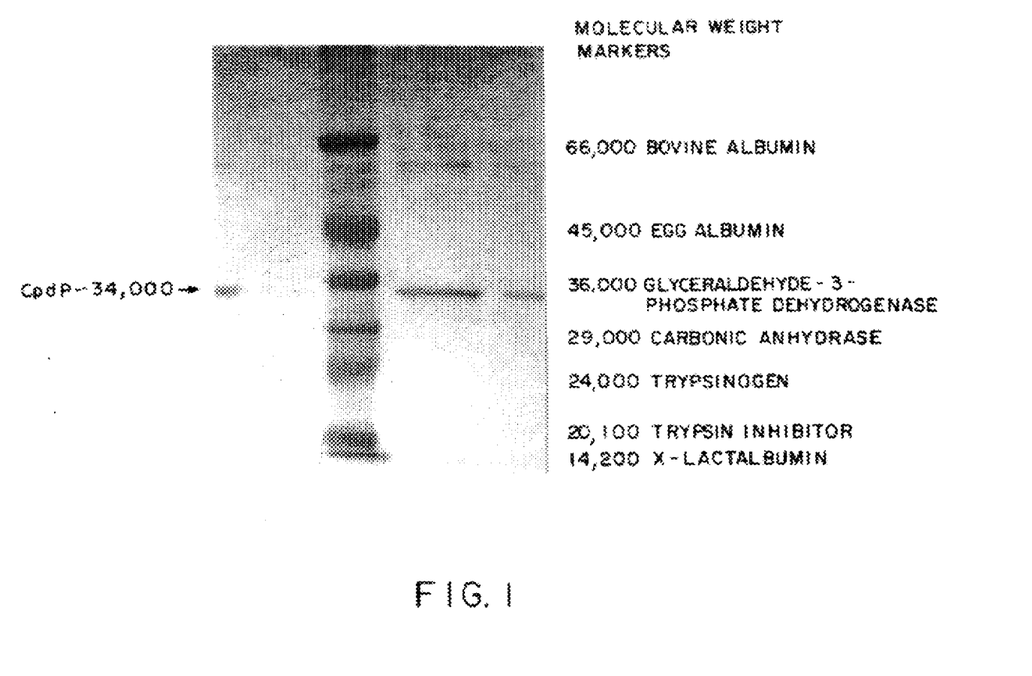
FIG. 1. Sodium dodecyl sulfate (SDS) polyacrylamide gel electrophoresis (PAGE) of 3':5'-cyclic AMP phosphodiesterase (CpdP, 34 kDa) purified from *V. fischeri* MJ-1 by the anion exchange and affinity chromatography procedure described in Example 1. 30 μl of sample, containing 10 μg total protein, was loaded and electrophoresed under the conditions described on the drawing. Other proteins, seen near the top of the lane, comprise less than 10% of the total loaded protein.

Proteins were visualized by SDS polyacrylamide gel electrophoresis, using a Hoefer SE250 (Hoefer Scientific Instruments, San Francisco, Calif.) mini gel apparatus and following the procedure described by Laemmli (Nature, 227:680–685 (1970)). As can be seen from FIG. 1, the 3':5'-cAMP phosphodiesterase has a molecular weight of about 34,000 on SDS-PAGE. The above protocol gives protein that is approximately 1000-fold purified compared to whole cells and that on SDS-PAGE looks to be about 90% pure.

EXAMPLE 2

Cold Acetone Purification of 3':5'-cAMP phosphodiesterase

Whole cells were pelleted, washed and resuspended in buffer and exposed to chloroform to release periplasm contents as described in Example 1. The supernatant, containing the periplasm contents, was fractionated with ammonium sulfate, as described in Example 1, and the 70% fraction was treated with cold acetone. Specifically, to the 70% ammonium sulfate fraction on ice, 0.75 volume (7.5 ml) of acetone at −20° C. was added, the solution was mixed by inversion a few times and placed at −20° C. for 45 min. The solution was then spun in a Sorvall RC-2B centrifuge in an SS-34 rotor for 5 min at −5° C. to −10° C. The pellet was resuspended in 10 ml of 10 mM Tris buffer at pH 8.0 (22° C.), assayed, found to have no activity, and discarded. 10 ml cold acetone (now 1.75 volumes of acetone) was then added to the supernatant, which contained the activity, and the incubation and spin were repeated. The pellet, which contained the activity, was resuspended in 10 ml of 10 mM Tris buffer at pH 8.0 (room temp.), assayed, and examined by SDS-polyacrylamide gel electrophoresis.

| Whole cells: | 2.1 µmol Pi released/min/ mg/protein |
|---|---|
| Periplasm extract: | 29 |
| Ammonium sulfate 70% fraction: | 109 |
| Acetone | 280 |

We interpret these results as indicating a 100-fold purification of the protein.

Figure 2:
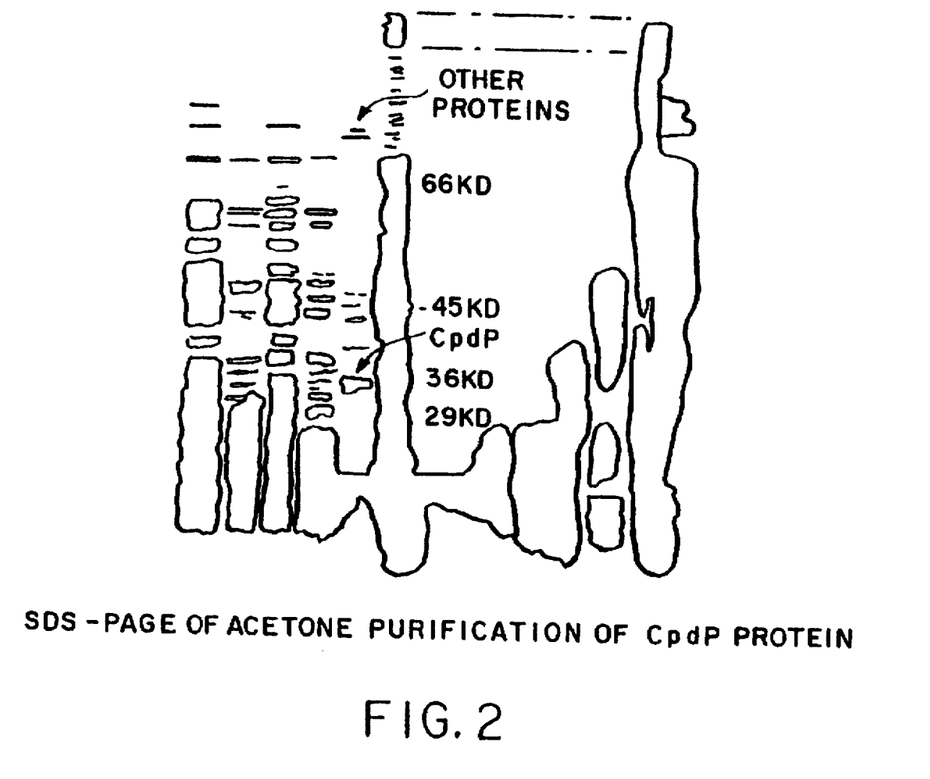
FIG. 2. Sodium dodecyl sulfate (SDS) polyacrylamide gel electrophoresis (PAGE) of 3':5'-cyclic AMP phosphodiesterase (CpdP, 34 kDa) purified from *V. fischeri* MJ-1 by the cold acetone procedure described in Example 2. 30 μl of sample, containing 80 μg total protein, was loaded and electrophoresed under the conditions described on the drawing. Other proteins, seen near the top of the lane, comprise less than 50% of the total loaded protein.

The gel, FIG. 2, was loaded with 30 µl of protein suspension, containing 80 µg of protein. Visual inspection of the gel indicates that protein is approximately 50% pure. Scanning densitometry analysis could also be used to quantify the protein and its percent purity.

EXAMPLE 3

Cloning of a Periplasmic 3':5'-cystic Nucleotide Phosphodiesterase Gene

To isolate the *V. fischeri* gene encoding periplasmic 3':5'cAMP phosphodiesterase, cells of *E. coli* AG-1 (Bullock et al., Biotechniques, 5:376–379 (1987)) were transformed with a gene library of *V. fischeri* MJ-1 (Rudy et al., Biol. Bull., 151:574–586 (1976)) chromosomal DNA constructed in pSUP102 (Simon et al., Meth. Enzymol., 118:640–659 (1980)) and plated on *E. coli* minimal medium (50 mM Tris-HCl, 50 mM NaCl, 1 mM $M_gSO^4$, 1 mM $CaCl_2$, 0.05 mM thiamine, 0.005% yeast extract (Difco), and 0.005% tryptone (Difco), pH 7.4, 15 g/l agar) agar plates containing cAMP (5 mM) as the sole carbon and energy source and chloramphenical (30 µg/ml). The genomic library of DNA from *V. fischeri* MJ-1 was prepared essentially as described by Sambrook et al. (1989) and Silhavy et al. (*Experiments with Gene Cloning*, Cold Spring Laboratory (1986)). Purified chromosomal DNA was partially digested with Sau3A1, size fractionated on a 0.7% agarose-TAE gel, and the portion of the gel containing the 10–15 kb size range of DNA was isolated. The DNA was electroeluted from the gel slice, purified by phenol extraction and ethanol precipitation, and then ligated into the BamH1 site of pSUP102 (Simon et al., Meth. Enzymol., 118:640–659 (1986)). The library was recovered by transformation of E. coli AG-1, with selection on LB agar (Silhavy et al., supra) containing chloramphenicol (30 μg/ml). Initial attempts at isolating the gene, by plating the transformed E. coli AG-1 cells on ECM-cAMP agar supplemented with $K_2HPO_4$ and $NH_4Cl$, were unsuccessful. In other work, however, we had noted that growth of V. fischeri on cAMP was suppressed somewhat in minimal medium supplemented with $K_2HPO_4$ and $NH_4Cl$ compared to minimal medium lacking these constituents. In accordance with this observation, the transformed E. coli AG-1 cells were plated on ECM-cAMP lacking $K_2HPO_4$ and $NH_4Cl$. In this case, several colonies arose in two days at 37° C.; all were found by restriction endonuclease digestion of their plasmid DNA to contain a similar 10–13-kilobase (kb) region of V. fischeri DNA. One clone, pMER120, which contained approximately 12 kb of V. fischeri DNA, was chosen for further study.

AG-1 containing pMER120 grew well in ECM-cAMP broth (lacking $K_2HPO_4$ and $NH_4Cl$), whereas AG-1 containing pSUP102 did not grow in this medium but did grow in ECM containing glucose, $K_2HPO_4$ and $NH_4Cl$. When E. coli AG-1 was re-transformed with pMER120 and plated on selective medium, an equal number of colonies arose on ECM-cAMP agar plates containing chloramphenical as arose on LB agar plates containing chloramphenicol. Consistent with growth on cAMP, AG-1 containing pMER120 expressed periplasmic CPDase activity, as determined by enzyme assays on intact cells (Dunlap et al., supra), at levels similar to those in V. fischeri. E. coli AG-1 containing pSUP102, however, exhibited no detectable periplasmic CPDase activity. By these criteria, we ascertained that the cloned V. fischeri DNA in pMER120 contained the gene encoding periplasmic CPDase.

We designate the gene for the V. fischeri periplasmic CPDase provisionally as cpdP, with P as a mnemonic for periplasmic. This designation accords with the designation given the gene (cpdA), which has not yet been cloned, of the cytoplasmic CPDase of Salmonella typhimurium (Alper and Ames, supra) and with the designation given the cloned gene (cpdB) encoding the periplasmic 2':3'-cAMP phosphodiesterase of E. coli (Beacham and Garrett, J. Gen. Micro., 119:31–34 (1980)).

Nucleotide sequence of the V. fischeri cpdP gene.

Figure 3:
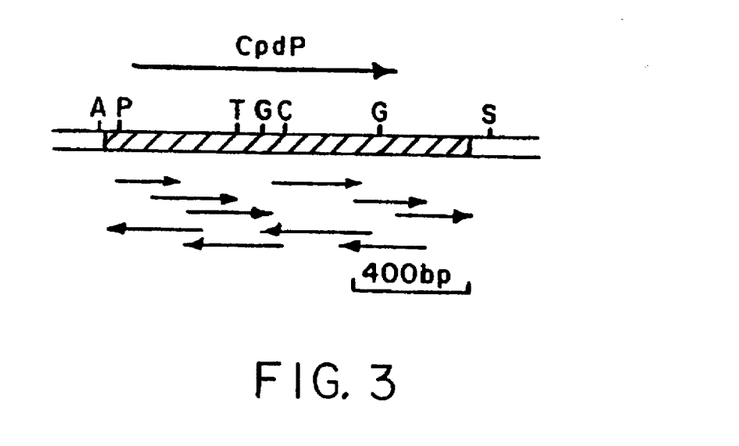
Figure 4:
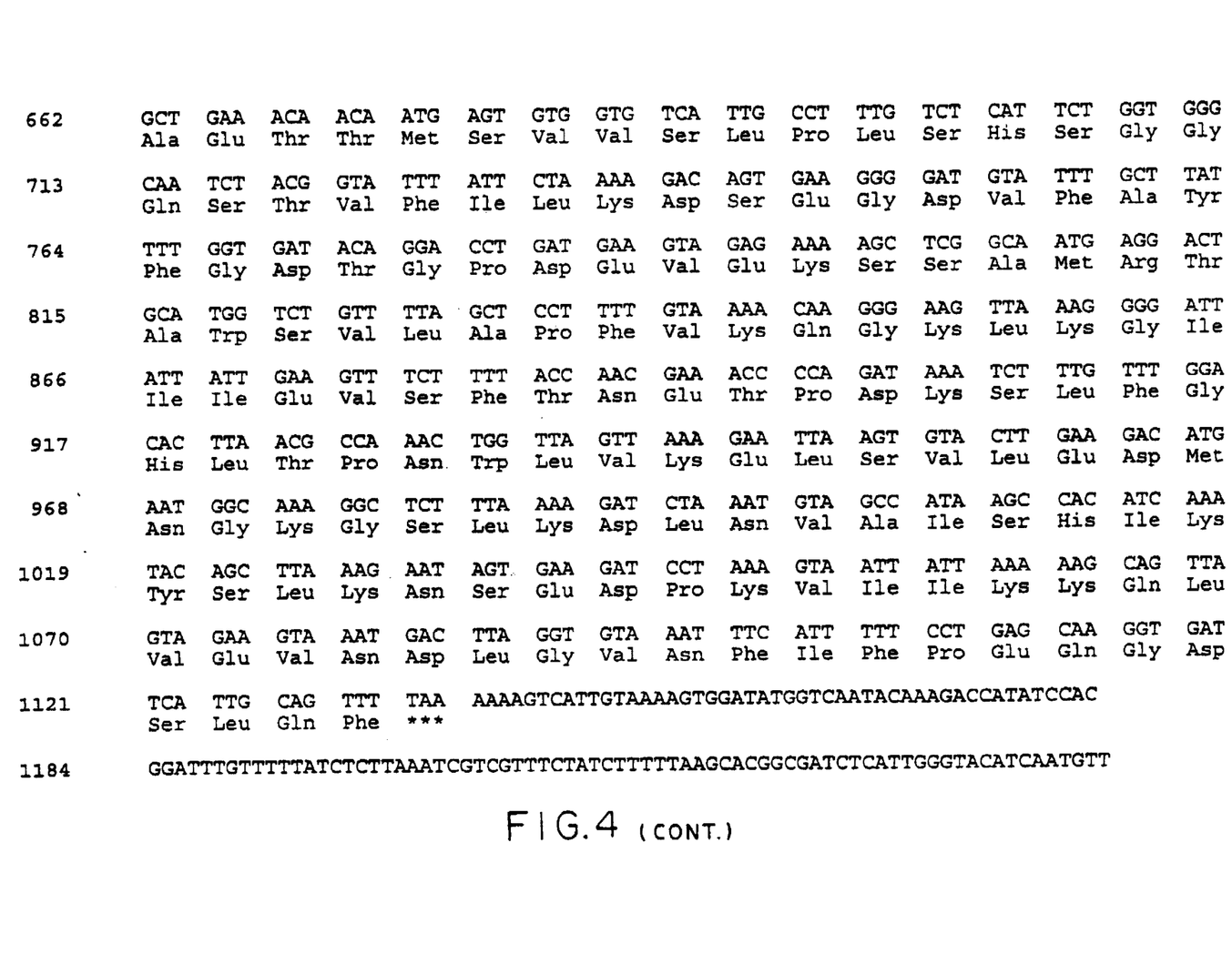

The DNA sequence of the 1.26 kb of V. fischeri DNA contained in pMER013 [pGEM®-72f(+)] was determined bidirectionally with SP6 and T7 primers and with primers designed for regions internal to the cloned DNA by the dideoxy termination method of Sanger et al. (Proc. Natl. Acad. Sci., 74:5463–5467 (1977)). A partial restriction map and the sequencing strategy are shown in FIG. 3. DNA sequence analysis was performed with the MacDNASIS Pro 1.01 package (national Bioscience, Plymouth, Minn.) Translation of the DNA sequence revealed one open reading frame, beginning at position 143 (ATG) and ending at position 1133 (TAA), specifying a protein of 330 amino acid residues and a deduced molecular weight of 36,087 (FIG. 4). The portion of the 12-kb insert DNA encoding CpdP (pMER120) was defined to 1.26 kb (pMER013) by standard subcloning and endonuclease III digestion procedures.

The recombinant enzyme can be purified to a similar degree of purity by the methods described in Examples 1 and 2.

What is claimed:

1. A periplasmic 3':5'-cyclic AMP phosphodiesterase substantially pure at a 50% level obtainable from *Vibrio fischeri*.

2. The phosphodiesterase of claims 1, wherein the phosphodiesterase has a molecular weight of about 34,000 on SDS-PAGE.

3. A periplasmic 3':5'-cyclic AMP phosphodiesterase comprising the amino acid sequence encoded by facet 43-1132 of SEQ ID NO:1.

4. The phosphodiesterase of claim 1, wherein said phosphodiesterase is obtained from *Vibrio fischeri*.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1257 base pairs
        ( B ) TYPE: nucleic acid
        ( C ) STRANDEDNESS: unknown
        ( D ) TOPOLOGY: unknown     ( i i ) MOLECULE TYPE: protein     ( i x ) FEATURE:
        ( A ) NAME/KEY: CDS
        ( B ) LOCATION: 143..1132

( x i ) SEQUENCE DESCRIPTION: SEQ ID NO:1:

```
AGTAGAACTA  TCAAATTCTG  TGGAGCATAC  CGCTTATAAT  TACCTTCTTA  TCAATAGTCT         60

TAAATATTTA  ATACATCATT  CATTTATCTC  ATTGTATTAT  CTGATTGAGC  ACAAGGGTGT        120

GCAGTATTAT  TTAAGGTTGG  AT ATG TTT AAA AAT AAA TTA GCA GTG TTA TTT           172
              Met Phe Lys Asn Lys Leu Ala Val Leu Phe
               1               5                  10

ACG TGT TTG TCT GTA TTT TCT TTT TCG GCT CAA TCT GGG AGT TTT GAT              220
Thr Cys Leu Ser Val Phe Ser Phe Ser Ala Gln Ser Gly Ser Phe Asp
              15                  20                  25

ACC GTT ACG TTA GGG AGT AAA GGT GGG ATT CAA GAT GGT AAT TTA ACG              268
Thr Val Thr Leu Gly Ser Lys Gly Gly Ile Gln Asp Gly Asn Leu Thr
```

|  |  |  |  |  |  |  |  |  |  |  |  |  |  |  |  |
|---|---|---|---|---|---|---|---|---|---|---|---|---|---|---|---|
|  |  |  | 30 |  |  |  |  | 35 |  |  |  |  | 40 |  |  |
| GCT | TTT | TTA | ATT | AAA | AGT | GAG | GCG | GAT | TCT | AAT | TTT | GTT | ATG | CTT | GAT |
| Ala | Phe | Leu | Ile | Lys | Ser | Glu | Ala | Asp | Ser | Asn | Phe | Val | Met | Leu | Asp |
|  |  |  | 45 |  |  |  |  | 50 |  |  |  |  | 55 |  |  |

316

| GCA | GGT | TCT | GTT | GTT | AAT | GGA | TTA | ATT | GTT | TCA | GAG | CAG | AAA | GGA | GCG |
|---|---|---|---|---|---|---|---|---|---|---|---|---|---|---|---|
| Ala | Gly | Ser | Val | Val | Asn | Gly | Leu | Ile | Val | Ser | Glu | Gln | Lys | Gly | Ala |
|  | 60 |  |  |  |  | 65 |  |  |  |  | 70 |  |  |  |  |

364

| TTT | AAA | GAT | ATT | ACC | GTC | CCA | GAT | AGT | TCG | CCT | TAC | ACC | AAA | GTA | GGT |
|---|---|---|---|---|---|---|---|---|---|---|---|---|---|---|---|
| Phe | Lys | Asp | Ile | Thr | Val | Pro | Asp | Ser | Ser | Pro | Tyr | Thr | Lys | Val | Gly |
| 75 |  |  |  |  | 80 |  |  |  |  | 85 |  |  |  |  | 90 |

412

| TAC | CTA | TTA | AAG | GAT | AGG | ATT | AAG | GGC | TAC | TTT | ATT | AGT | CAT | GCT | CAT |
|---|---|---|---|---|---|---|---|---|---|---|---|---|---|---|---|
| Tyr | Leu | Leu | Lys | Asp | Arg | Ile | Lys | Gly | Tyr | Phe | Ile | Ser | His | Ala | His |
|  |  |  |  | 95 |  |  |  |  | 100 |  |  |  |  | 105 |  |

460

| TTA | GAC | CAT | GTT | GCT | GGT | TTA | ATT | ATC | TCT | TCT | CCT | GAT | GAC | AGT | AAA |
|---|---|---|---|---|---|---|---|---|---|---|---|---|---|---|---|
| Leu | Asp | His | Val | Ala | Gly | Leu | Ile | Ile | Ser | Ser | Pro | Asp | Asp | Ser | Lys |
|  |  |  | 110 |  |  |  |  | 115 |  |  |  |  | 120 |  |  |

508

| AAA | CCG | ATA | TAT | GGA | TTA | GCA | GCG | ACA | AAT | AAA | GAT | CTC | ATG | AAG | AAT |
|---|---|---|---|---|---|---|---|---|---|---|---|---|---|---|---|
| Lys | Pro | Ile | Tyr | Gly | Leu | Ala | Ala | Thr | Asn | Lys | Asp | Leu | Met | Lys | Asn |
|  |  | 125 |  |  |  |  | 130 |  |  |  |  | 135 |  |  |  |

556

| TAC | TTT | AAT | TGG | TCA | GCA | TGG | CCT | AAT | TTT | GGT | AAC | AAA | GGT | GAA | GGC |
|---|---|---|---|---|---|---|---|---|---|---|---|---|---|---|---|
| Tyr | Phe | Asn | Trp | Ser | Ala | Trp | Pro | Asn | Phe | Gly | Asn | Lys | Gly | Glu | Gly |
| 140 |  |  |  |  | 145 |  |  |  |  | 150 |  |  |  |  |  |

604

| TTT | AAA | CTG | AAC | AAA | TAC | AAT | TAT | GTG | GAT | CTT | CAA | CCG | GGC | GTT | TGG |
|---|---|---|---|---|---|---|---|---|---|---|---|---|---|---|---|
| Phe | Lys | Leu | Asn | Lys | Tyr | Asn | Tyr | Val | Asp | Leu | Gln | Pro | Gly | Val | Trp |
| 155 |  |  |  |  | 160 |  |  |  |  | 165 |  |  |  |  | 170 |

652

| AGT | CCG | GTA | GCT | GAA | ACA | ACA | ATG | AGT | GTG | GTG | TCA | TTG | CCT | TTG | TCT |
|---|---|---|---|---|---|---|---|---|---|---|---|---|---|---|---|
| Ser | Pro | Val | Ala | Glu | Thr | Thr | Met | Ser | Val | Val | Ser | Leu | Pro | Leu | Ser |
|  |  |  |  | 175 |  |  |  |  | 180 |  |  |  |  | 185 |  |

700

| CAT | TCT | GGT | GGG | CAA | TCT | ACG | GTA | TTT | ATT | CTA | AAA | GAC | AGT | GAA | GGG |
|---|---|---|---|---|---|---|---|---|---|---|---|---|---|---|---|
| His | Ser | Gly | Gly | Gln | Ser | Thr | Val | Phe | Ile | Leu | Lys | Asp | Ser | Glu | Gly |
|  |  |  | 190 |  |  |  |  | 195 |  |  |  |  | 200 |  |  |

748

| GAT | GTA | TTT | GCT | TAT | TTT | GGT | GAT | ACA | GGA | CCT | GAT | GAA | GTA | GAG | AAA |
|---|---|---|---|---|---|---|---|---|---|---|---|---|---|---|---|
| Asp | Val | Phe | Ala | Tyr | Phe | Gly | Asp | Thr | Gly | Pro | Asp | Glu | Val | Glu | Lys |
|  |  | 205 |  |  |  |  | 210 |  |  |  |  | 215 |  |  |  |

796

| AGC | TCG | GCA | ATG | AGG | ACT | GCA | TGG | TCT | GTT | TTA | GCT | CCT | TTT | GTA | AAA |
|---|---|---|---|---|---|---|---|---|---|---|---|---|---|---|---|
| Ser | Ser | Ala | Met | Arg | Thr | Ala | Trp | Ser | Val | Leu | Ala | Pro | Phe | Val | Lys |
|  | 220 |  |  |  |  | 225 |  |  |  |  | 230 |  |  |  |  |

844

| CAA | GGG | AAG | TTA | AAG | GGG | ATT | ATT | ATT | GAA | GTT | TCT | TTT | ACC | AAC | GAA |
|---|---|---|---|---|---|---|---|---|---|---|---|---|---|---|---|
| Gln | Gly | Lys | Leu | Lys | Gly | Ile | Ile | Ile | Glu | Val | Ser | Phe | Thr | Asn | Glu |
| 235 |  |  |  |  | 240 |  |  |  |  | 245 |  |  |  |  | 250 |

892

| ACC | CCA | GAT | AAA | TCT | TTG | TTT | GGA | CAC | TTA | ACG | CCA | AAC | TGG | TTA | GTT |
|---|---|---|---|---|---|---|---|---|---|---|---|---|---|---|---|
| Thr | Pro | Asp | Lys | Ser | Leu | Phe | Gly | His | Leu | Thr | Pro | Asn | Trp | Leu | Val |
|  |  |  |  | 255 |  |  |  |  | 260 |  |  |  |  | 265 |  |

940

| AAA | GAA | TTA | AGT | GTA | CTT | GAA | GAC | ATG | AAT | GGC | AAA | GGC | TCT | TTA | AAA |
|---|---|---|---|---|---|---|---|---|---|---|---|---|---|---|---|
| Lys | Glu | Leu | Ser | Val | Leu | Glu | Asp | Met | Asn | Gly | Lys | Gly | Ser | Leu | Lys |
|  |  |  | 270 |  |  |  |  | 275 |  |  |  |  | 280 |  |  |

988

| GAT | CTA | AAT | GTA | GCC | ATA | AGC | CAC | ATC | AAA | TAC | AGC | TTA | AAG | AAT | AGT |
|---|---|---|---|---|---|---|---|---|---|---|---|---|---|---|---|
| Asp | Leu | Asn | Val | Ala | Ile | Ser | His | Ile | Lys | Tyr | Ser | Leu | Lys | Asn | Ser |
|  |  | 285 |  |  |  |  | 290 |  |  |  |  | 295 |  |  |  |

1036

| GAA | GAT | CCT | AAA | GTA | ATT | ATT | AAA | AAG | CAG | TTA | GTA | GAA | GTA | AAT | GAC |
|---|---|---|---|---|---|---|---|---|---|---|---|---|---|---|---|
| Glu | Asp | Pro | Lys | Val | Ile | Ile | Lys | Lys | Gln | Leu | Val | Glu | Val | Asn | Asp |
|  | 300 |  |  |  |  | 305 |  |  |  |  | 310 |  |  |  |  |

1084

| TTA | GGT | GTA | AAT | TTC | ATT | TTT | CCT | GAG | CAA | GGT | GAT | TCA | TTG | CAG | TTT |
|---|---|---|---|---|---|---|---|---|---|---|---|---|---|---|---|
| Leu | Gly | Val | Asn | Phe | Ile | Phe | Pro | Glu | Gln | Gly | Asp | Ser | Leu | Gln | Phe |
| 315 |  |  |  |  | 320 |  |  |  |  | 325 |  |  |  |  | 330 |

1132

TAAAAAAGTC ATTGTAAAAG TGGATATGGT CAATACAAAG ACCATATCCA CGGATTTGTT    1192

TTTATCTCTT AAATCGTCGT TTCTATCTTT TTAAGCACGG CGATCTCATT GGGTACATCA    1252

ATGTT    1257